(12) United States Patent
Kerr et al.

(10) Patent No.: US 8,476,424 B2
(45) Date of Patent: Jul. 2, 2013

(54) REMOVAL OF ACIDS FROM TERTIARY AMIDE SOLVENTS

(75) Inventors: John Kerr, South Croyden (GB); Robert Jansen, Portella LRS (PT); Christian J. Isaac, Fort Dodge, IA (US); James Edwin Wiley, Jr., Daphne, AL (US); Duane A. Leinhos, Satsuma, AL (US)

(73) Assignee: Tate & Lyle Technology Limited, London (GB)

( * ) Notice: Subject to any disclaimer, the term of this patent is extended or adjusted under 35 U.S.C. 154(b) by 805 days.

(21) Appl. No.: 12/403,762

(22) Filed: Mar. 13, 2009

(65) Prior Publication Data

US 2009/0259034 A1 Oct. 15, 2009

Related U.S. Application Data

(60) Provisional application No. 61/070,070, filed on Mar. 20, 2008.

(51) Int. Cl.
*C07H 1/06* (2006.01)
*C07H 5/02* (2006.01)

(52) U.S. Cl.
USPC .................... 536/123.13; 536/127

(58) Field of Classification Search
None
See application file for complete search history.

(56) References Cited

U.S. PATENT DOCUMENTS

| | | | |
|---|---|---|---|
| 4,362,869 A | 12/1982 | Jenner | |
| 4,380,476 A | 4/1983 | Mufti | |
| 4,405,654 A | 9/1983 | Lee | |
| 4,783,526 A | 11/1988 | O'Brien | |
| 4,826,962 A | 5/1989 | Rathbone | |
| 4,889,928 A | 12/1989 | Simpson | |
| 4,950,746 A | 8/1990 | Navia | |
| 4,980,463 A | 12/1990 | Walkup et al. | |
| 5,023,329 A | 6/1991 | Neiditch et al. | |
| 5,034,551 A | 7/1991 | Vernon et al. | |
| 5,089,608 A | 2/1992 | Walkup et al. | |
| 5,128,248 A | 7/1992 | Dordick | |
| 5,141,860 A | 8/1992 | Bornemann | |
| 5,270,071 A | 12/1993 | Sharp | |
| 5,272,137 A | 12/1993 | Blase | |
| 5,298,611 A | 3/1994 | Navia | |
| 5,354,902 A | 10/1994 | Merciadez | |
| 5,374,659 A | 12/1994 | Gowan | |
| 5,384,311 A | 1/1995 | Antenucci | |
| 5,397,588 A | 3/1995 | Antenucci | |
| 5,409,907 A | 4/1995 | Blase | |
| 5,426,220 A | 6/1995 | Baniel et al. | |
| 5,440,026 A | 8/1995 | Kahn | |
| 5,470,969 A | 11/1995 | Sankey et al. | |
| 5,498,709 A | 3/1996 | Navia et al. | |
| 5,530,106 A | 6/1996 | Navia | |
| 5,593,696 A | 1/1997 | McNally | |
| 5,621,005 A | 4/1997 | Gowan | |
| 5,658,919 A | 8/1997 | Ratnaraj | |
| 5,674,522 A | 10/1997 | Shah | |
| 5,817,340 A | 10/1998 | Roche | |
| 5,876,759 A | 3/1999 | Gowan | |
| 5,977,349 A | 11/1999 | Catani | |
| 6,080,481 A | 6/2000 | Ochs | |
| 6,090,401 A | 7/2000 | Gowan | |
| 6,176,935 B1 | 1/2001 | Brahmbhatt | |
| 6,211,246 B1 | 4/2001 | Gelotte | |
| 6,258,381 B1 | 7/2001 | Luber | |
| 6,265,012 B1 | 7/2001 | Shamil | |
| 6,277,409 B1 | 8/2001 | Luber | |
| 6,646,121 B2 | 11/2003 | El Kabbani | |
| 6,723,877 B1 | 4/2004 | Maliszewskyj | |
| 6,809,198 B2 | 10/2004 | El Kabbani | |
| 6,890,581 B2 * | 5/2005 | Vernon et al. | 426/658 |
| 6,939,962 B2 | 9/2005 | Clark | |
| 6,943,248 B2 | 9/2005 | Catani | |
| 6,998,144 B2 | 2/2006 | Merkel | |
| 6,998,480 B2 | 2/2006 | Catani | |
| 7,049,435 B2 | 5/2006 | Catani | |
| 2002/0157937 A1 | 10/2002 | Cockrem et al. | |
| 2004/0030124 A1 | 2/2004 | Catani | |
| 2006/0188629 A1 | 8/2006 | Liesen | |
| 2006/0205936 A1 | 9/2006 | Jia | |
| 2006/0276639 A1 | 12/2006 | Fry | |
| 2007/0015916 A1 | 1/2007 | Kabbani | |
| 2007/0100139 A1 | 5/2007 | Fry | |
| 2007/0160732 A1 | 7/2007 | Deshpande | |
| 2007/0227897 A1 | 10/2007 | Li | |
| 2007/0270583 A1 | 11/2007 | Ratnam | |
| 2008/0227971 A1 | 9/2008 | Leinhos | |

FOREIGN PATENT DOCUMENTS

| | | |
|---|---|---|
| DE | 10260085 | 7/2004 |
| EP | 0043649 | 1/1982 |

(Continued)

OTHER PUBLICATIONS

Qin, Y. et al., Ind. Eng. Chem. Res., "Pervaporation Membranes That Are Highly Selective for Acetic Acid over Water", 2003, vol. 42, pp. 582-595.*

(Continued)

*Primary Examiner* — Layla Bland
*Assistant Examiner* — Bahar Craigo
(74) *Attorney, Agent, or Firm* — RatnerPrestia

(57) ABSTRACT

A method of removing a carboxylic acid from a liquid that contains a tertiary amide solvent includes a step of contacting the liquid with an extraction medium comprising an amine. The amine is immiscible with both water and the tertiary amide solvent, and the contacting step forms a de-acidified phase containing the tertiary amide solvent and a phase containing the extraction medium and the carboxylic acid. Both the liquid that contains the tertiary amide solvent and the de-acidified phase may also contain a sucrose-6-acylate.

22 Claims, 2 Drawing Sheets

FOREIGN PATENT DOCUMENTS

| | | |
|---|---|---|
| EP | 0409549 | 1/1991 |
| EP | 0708110 | 4/1996 |
| GB | 1426018 | 2/1976 |
| WO | WO 0014052 | 3/2000 |
| WO | WO 02/074403 | 9/2002 |
| WO | 03076453 | 9/2003 |
| WO | 03076454 | 9/2003 |
| WO | 2005090374 | 9/2005 |
| WO | 2005090376 | 9/2005 |
| WO | 2006061855 | 6/2006 |
| WO | 2006130169 | 12/2006 |
| WO | 2007017899 | 2/2007 |
| WO | 2007023505 | 3/2007 |
| WO | 2007052304 | 5/2007 |
| WO | 2008004246 | 1/2008 |
| WO | 2008091539 | 7/2008 |

OTHER PUBLICATIONS

Chemical Land 21, "dibenzylamine"; also available at http://chemicalland21.com/specialtychem/perchem/DIBENZYLAMINE.htm; last accessed Mar. 26, 2012.*

Clark, Jim, "Introducing Amines"; copyright 2004; also available at http://www.chemguide.co.uk/organicprops/amines/background.html; last accessed Mar. 26, 2012.*

Sigma Aldrich, Material Safety Data Sheet, "N,N-Dimethylformamide"; last revised Jan. 17, 2012.*

Fisher Scientific, Safety Data Sheet: Trioctylamine, revised Dec. 22, 2006; 4 pages total.*

Smallwood, Ian, Solvent Recovery Handbook, Second Edition, Blackwell Publishing 2002, pp. 404, 405 and 407.*

Tamada, J. A. et al., Ind. Eng. Chem. Res., "Extraction of Carboxylic Acids with Amine Extractants. 1. Equilibria and Law of Mass Action Modeling", 1990, vol. 29, pp. 1319-1326.*

Ovens, Dr. Annabel, European Search Report, Sep. 17, 2008, 3 pp, London, UK.

Roider, Josef, et al.; International Search Report; Jun. 8, 2009; 15 pp; European Patent Office, Rijswijk, Netherlands.

Schierbaum, Burkhard, et al.; "Isolation of Carboxylic Acids From Aqueous Solutions by Extraction with Dialkylcarboxylic Amides/Trialkylamines"; Chem. Eng. Technol.; 1999; pp. 37-41; vol. 22; US.

Ault, A.. Techniques and Experiments for Organic Chemistry, 1987, pp. 43-44.

Chen et al., Ind. Engg. Chem. Res., 1999, 38, 1605-1610.

DeSilva, F., Water Quality Products, 2006, 11(4), pp. 1-3.

Grant et al, Chemical Dictionary, 1987, p. 122.

Merck Index, 1996, p. 549.

Smith et al, Food Additives Databook, 2003, p. 988.

The Free Dictionary, McGraw-Hill, 2003, pp. 1-2.

* cited by examiner

REMOVAL OF ACIDS FROM TERTIARY AMIDE SOLVENTS

CROSS REFERENCE TO RELATED APPLICATIONS (IF APPLICABLE)

This application claims priority of U.S. Provisional Patent Application No. 61/070,070, filed Mar. 20, 2008, the entirety of which is incorporated herein by reference.

BACKGROUND OF THE INVENTION

Sucralose (4,1',6'-trichloro-4,1',6'-trideoxygalactosucrose), a high-intensity sweetener made from sucrose, can be used in many food and beverage applications.

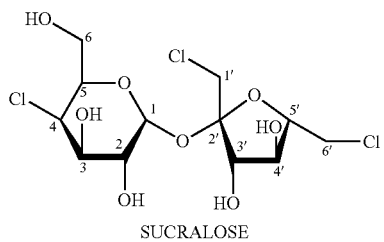

SUCRALOSE

A number of different synthesis routes for the preparation of sucralose have been developed in which the reactive hydroxyl in the 6 position is first blocked with an acyl group to form a sucrose-6-acylate. The acyl group is typically acetyl or benzoyl, although others may be used. The sucrose-6-acylate is then chlorinated to replace the hydroxyls at the 4, 1' and 6' positions to produce 4,1',6'-trichloro-4,1',6'-trideoxygalactosucrose 6-acylate (referred to herein as sucralose-6-acylate), followed is by hydrolysis to remove the acyl substituent and thereby produce sucralose. Several synthesis routes for formation of the sucrose-6-acylates involve tin-mediated acylation reactions, with illustrative examples being disclosed in U.S. Pat. Nos. 4,950,746; 5,023,329; 5,089,608; 5,034,551; and 5,470,969, all of which are incorporated herein by reference.

Various chlorinating agents may be used to chlorinate the sucrose-6-acylate, and most commonly a Vilsmeier-type salt such as Arnold's Reagent will be used. One suitable chlorination process is disclosed by Walkup et al. (U.S. Pat. No. 4,980,463), incorporated herein by reference. This process uses a tertiary amide, typically N,N-dimethyl formamide ("DMF"), as the chlorination reaction solvent. After the chlorination is complete, adducts of Arnold's reagent on the base sucrose moiety and excess chlorinating reagent are neutralized ("quenched") with aqueous base to provide the sucralose-6-acylate in an aqueous solution, accompanied by the tertiary amide solvent and salts resulting from reactions of the chlorination reagent. The sucralose-6-acylate is then deacylated to produce sucralose. One suitable deacylation process is taught by Navia et al, U.S. Pat. No. 5,498,709, the entire disclosure of which is incorporated herein by reference.

SUMMARY OF THE INVENTION

In one aspect, the invention provides a method of removing a carboxylic acid from a liquid comprising a tertiary amide solvent, the method comprising a step of contacting the liquid comprising the tertiary amide solvent and the carboxylic acid with an extraction medium comprising an amine that is immiscible with both water and the tertiary amide solvent, thereby forming a phase comprising de-acidified tertiary amide solvent and a phase comprising the extraction medium and the carboxylic acid.

DETAILED DESCRIPTION OF THE INVENTION

Figure 1:
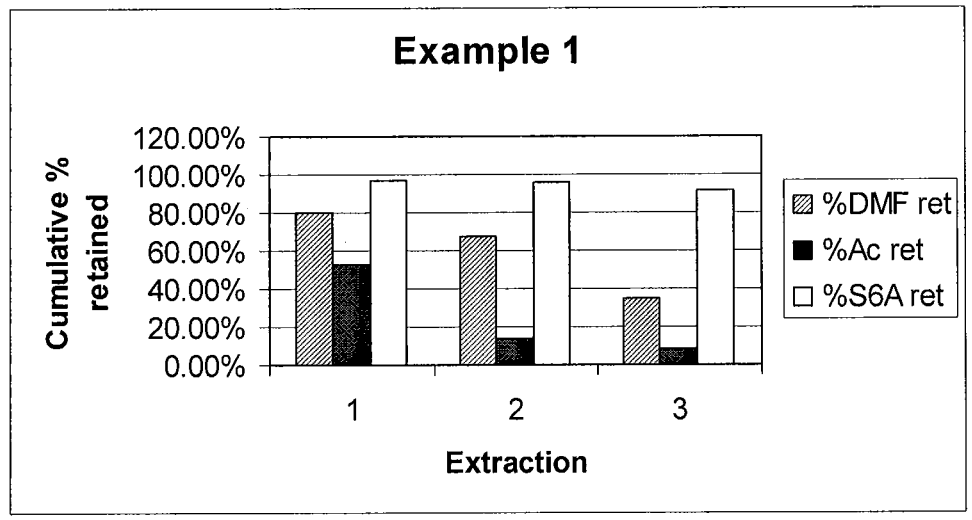
FIG. 1 shows the percentages of acetic acid and sucrose-6-acetate retained in a DMF sample after each of three sequential extractions with an extraction medium according to the invention.

The inventors have found that, during the manufacture of sucralose, significant amounts of lower carboxylic acids may be produced as side products or byproducts during various phases of the synthesis sequence. These typically include acetic acid, in the case where sucrose-6-acetate is used as an intermediate in the process, and/or formic acid, which can form by hydrolysis of DMF if that solvent is used in the process, e.g., to form a Vilsmeier-type salt. For simplicity, the discussion hereinafter will refer to the removal of these acids. However, other acids may be present in addition or instead, depending on the specific synthesis route taken in making the sucralose. Other exemplary acids include $C_3$-$C_7$ monocarboxylic acids, for example benzoic acid. The removal of any carboxylic acid from a tertiary amide solvent is contemplated according to the invention. Unfortunately, carboxylic acids may contribute to the corrosion of manufacturing equipment, and thus, their presence is problematic. In particular, significant amounts of these acids end up in the tertiary amide solvent that is used and subsequently recovered, purified and recycled in the process.

The invention provides methods of removing such acids from tertiary amide solvents. Nonlimiting examples of tertiary amide solvents from which acids may be removed include N,N-dimethyl formamide (DMF), N,N-dimethyl acetamide, and N-methyl-2-pyrrolidone. For simplicity, the present invention will be described with respect to the use of DMF as the solvent used for sucralose synthesis, and the removal of carboxylic acids from DMF, but the removal of acids from any tertiary amide solvent is within the scope of this invention.

Much of the removal of acids such as acetic and/or formic acid from DMF may be achieved by distillation. However, the inventors have found that it is desirable to first minimize the wt % of carboxylic acids in the distillation feed as much as possible, because these acids can concentrate in the distillation apparatus, causing a low pH and consequent corrosion of the apparatus. This preliminary acid removal is preferably performed in such a way as to minimize decomposition of the DMF, as well as to allow recovery of the acids for reuse in the process, for example for pH adjustment.

Accordingly, the invention provides removal of carboxylic acids from a liquid comprising DMF by a method comprising the following steps. Acetic acid and formic acid will be used as an example.

(i) Acetic acid and formic acid are extracted from the DMF using an amine-containing extraction medium.

(ii) The extraction medium is purified by washing it with water to extract DMF.

(iii) The purified extraction medium is washed with hot water to extract the acetic and/or formic acid to give (a) a low-pH aqueous stream containing acetic and/or formic acid (which may optionally be used for any of a variety of purposes, such as the neutralization of high-pH waste from the sucralose synthesis process), and (b) a partially de-acidified extraction medium.

(iv) The partially de-acidified extraction medium is further washed with an aqueous base to further remove acetic and/or formic acid and thereby give a substantially de-acidified extraction medium. The extraction medium may then optionally be recycled for use in step (i).

In step (i), the liquid comprising the DMF typically contains at least 60 wt % DMF, more typically at least 70 wt % DMF, and most typically at least 80 wt %, DMF. The remainder of the liquid typically comprises water and various salts, typically in roughly equal amounts. Step (i) typically extracts at least 80 wt % of the acids from the DMF, more typically at least 85 wt %, and most typically at least 90 wt %. The result is a de-acidified phase comprising DMF and a phase comprising the extraction medium and carboxylic acid. Typically, the de-acidified phase is further treated to produce a purified DMF. In some embodiments, this involves routing the DMF to an evaporator to remove nonvolatile materials. For example, various carbohydrate products and byproducts may be including in this nonvolatile material. Various kinds of evaporator may be suitable, including for example a mechanical vapor recompression evaporator or a forced circulation evaporative system. The volatile component exiting the evaporator is then condensed, and may then be distilled or further evaporated and condensed to provide essentially pure DMF as an overhead fraction and the extraction medium component(s) as a bottoms fraction. The bottoms fraction may optionally be routed back for reuse in step (i), and the DMF may be routed back for use in the sucralose synthesis sequence, such as in the chlorination step.

Step (ii) is typically performed in a temperature range from 5° C. to 50° C., more typically from 10° C. to 40° C., and most typically from 15° C. to 30° C. Ambient temperature is usually used. The resulting aqueous phase, containing DMF extracted from the extraction medium, may be routed back to the extractor of step (i) to improve recovery of the DMF.

Step (iii) is typically performed at a temperature of at least 50° C., more typically at least 60° C., and most typically at least 70° C. The temperature will typically be at most 90° C., more typically at most 85° C., and most typically at most 80° C. Typically, this step removes about 90% of the acid from the extraction medium.

In step (iv), the aqueous base is typically adjusted to a pH between 9 and 11.5. In some embodiments, pH-adjusted saturated aqueous sodium acetate is used in this step. This step typically results in removal of at least 98 wt % of the acids originally present, more typically at least 99.5 wt %.

In some embodiments of the invention, DMF that has been pre-purified by the methods of this invention may be used to dissolve sucrose for ultimate conversion to sucralose, for example via formation of a sucrose-6-acylate, chlorination of the sucrose-6-acylate, and deacylation of the resulting sucralose-6-acylate to form sucralose. In other embodiments, extraction methods such as described herein may be employed on solutions of sucrose derivatives in DMF. For example, it may be desirable to remove acids from solutions of sucrose-6-acylates in DMF prior to their chlorination to form sucralose-6-acylates (and ultimately, the production of sucralose), and such solutions may be treated to remove carboxylic acids using an extraction medium according to the invention. Examples 1 and 2 relate to such a process. After such extraction, the sucrose-6-acylate may be chlorinated according to known methods (e.g., with Arnold's reagent) to produce sucrose-6-acylate, which may subsequently be deacylated to produce sucralose.

Suitable equipment for performing the extractions of this invention includes any known in the chemical engineering art. For example, countercurrent mixer-settler units may be used. Other suitable extraction techniques include batteries of single stage centrifuges or multi-stage centrifuges, such as Robatel BXP series, Podbielniak centrifugal extractors. Also suitable are counter current column technologies such as Scheibel and Karr extraction columns. In some embodiments, simple batch extractions followed by decanting may be used. Packed/sieve tray columns may also be used.

Extraction Medium

The composition of the extraction medium is chosen such that it is capable of both drawing carboxylic acids out of the DMF and releasing the acids to a water or aqueous base wash. The extraction medium preferably does not contaminate the process solvent (e.g., DMF) in ways that interfere with the various synthesis steps and processes involved in sucralose manufacturing process. Preferably, the extraction medium is recoverable and recyclable for repeated use in the process.

Extraction media according to the invention comprise an amine, and may consist of a single component or a mixture of components, only one of which need be an amine. Any of a variety of amines may be used, provided that the amine is not miscible with water or DMF. In some embodiments, the amine has a melting point of at most 20° C., which will typically allow the amine to be used in the process as a liquid, thereby facilitating extraction. One suitable example is commercial grade trilaurylamine, which has a melting point of about 14° C. In some embodiments, the amine has a lower vapor pressure than DMF, which boils at 153° C. at 760 torr. That is, it either does not boil at all without decomposing, or it boils at a temperature higher than DMF, thus facilitating separation of the amine from DMF by distillation or evaporation/condensation. One suitable example is commercial grade trilaurylamine, which has a boiling point of about 450° C.

The amine is typically a monoamine, and typically it does not contain any heteroatoms other than the amine nitrogen atom. In some embodiments, the amine is according to the formula $NR^1R^2R^3$ where each of $R^1$, $R^2$ and $R^3$ is independently selected from the group consisting of H and $C_1$-$C_{20}$ linear or branched alkyl, cyclic, alicyclic, alkenyl, aryl, aralkyl, and alkaryl groups, provided that at least one of $R^1$, $R^2$ and $R^3$ is not H. The amine may be primary, secondary, or tertiary. Typically the amine is tertiary. Typically, each of $R^1$, $R^2$ and $R^3$ is a $C_7$-$C_{20}$ hydrocarbyl group. In some embodiments, each of $R^1$, $R^2$ and $R^3$ is an independently selected linear, branched or cyclic alkyl group. Nonlimiting examples of suitable $R^1$, $R^2$ and $R^3$ groups include straight chain or branched chain alkyl groups, such as heptyl, 2-ethylhexyl, octyl, nonyl, 3,5-dimethyloctyl, 3,7-dimethyloctyl, decyl, undecyl, dodecyl, tridecyl, tetradecyl, 3-methyl-10-ethyldodecyl, pentadecyl, hexadecyl, heptadecyl, octadecyl, nonadecyl, eicosyl, and cocoalkyl. Other suitable examples of $R^1$, $R^2$ and $R^3$ include cyclohexyl, cyclohexylmethyl, benzyl, pinyl, pinylmethyl, phenethyl, p-methylbenzyl, phenyl, tolyl, xylyl, naphthyl, ethylphenyl, methylnaphthyl, dimethylnaphthyl, 2-norbornyl, 2-bornyl, norbornylmethyl, and adamantyl. Typically, the total number of carbon atoms in $R^1$, $R^2$ and $R^3$ is at least 24, more typically at least 30, and most typically at least 36.

In some embodiments of the invention, the extraction medium comprises a mixture of the amine with an alcohol R¹OH, where R¹ is according to any of the embodiments described above and further comprises at least seven carbon atoms. The alcohol is not miscible with water or DMF. Typically, R¹ is an alkyl group, and typically it comprises at least ten carbon atoms. One example is dodecanol. The specific composition of the extraction medium is not critical, but typically it contains at least 20 wt % amine, more typically at least 30 wt %, and most typically at least 40 wt %. Neat amine may also be used. Typically, the extraction medium contains at most 80 wt %, more typically at most 70 wt %, and most typically at most 60 wt % of amine. The balance of the extraction medium is generally the alcohol, although other components may optionally be included. In some embodiments, the amine is trilaurylamine and the alcohol is dodecanol. In one particular embodiment, the extraction medium is about 50/50 wt/wt of trilaurylamine and dodecanol.

EXAMPLES

Figure 2:
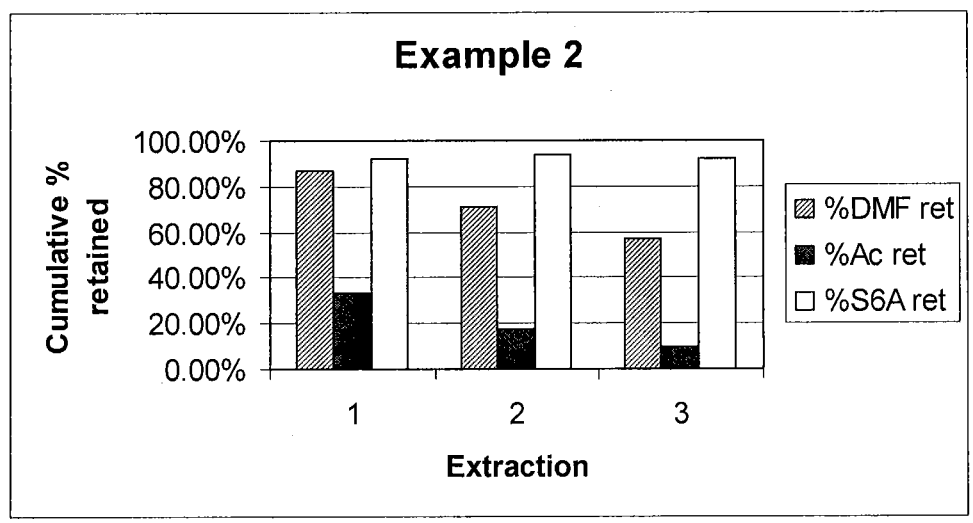
FIG. 2 shows the results of a larger scale extraction according to the invention.

Examples 1 and 2 exemplify methods of extracting acetic acid from a DMF sample containing carbohydrates. The results are depicted graphically in FIGS. 1 and 2, respectively, showing the percentages of each indicated component retained in the lower layer after each of three extractions with a mixture of dodecanol and trilaurylamine. As can be seen from the data, the methods of this invention allow effective removal of acetic acid from a solution of sucrose-6-acylate in DMF with very little loss of sucrose-6-acylate. DMF was measured by gas chromatography, acetic acid by ion chromatography, and sucrose-6-acetate by high performance liquid chromatography.

Example 1

Using a separatory funnel, a 25 g sample of a stream used in the manufacture of sucralose containing about 11 wt % of a mixture of acetylated sucroses (about 80 wt % of which was sucrose-6-acetate) as well as 46100 ppm acetic acid, 70.3% DMF, and about 14 wt % water was extracted with 25 g of an extraction medium consisting of a 1:1 by weight mixture of trilaurylamine and dodecanol. The sample contained 17.7 g DMF, 1.15 g acetic acid, and 2.1 g sucrose-6-acetate. The resultant upper (extraction medium) phase weighed 28.76 g. The lower (DMF) phase weighed 21.15 g and was assayed to contain 14.2 g DMF, 0.61 g acetic acid, and 2.03 g sucrose-6-acetate. This is designated the first lower phase.

A 16.82 g portion of the first lower phase was extracted with 17.5 g of the 1:1 trilaurylamine:dodecanol mixture. The portion of 1$^{st}$ lower phase used contained 11.3 g DMF, 0.48 g acetic acid, and 1.62 g sucrose-6-acetate. The resulting lower phase, designated the second lower phase, weighed 14.27 g and contained 9.54 g DMF, 0.122 g acetic acid, and 1.60 g sucrose-6-acetate. The upper phase weighed 20.09 g.

A 10.71 g portion of the second lower phase was extracted with 10.0 g of the 1:1 trilaurylamine:dodecanol mixture. The portion of 2$^{nd}$ lower phase used contained 7.16 g DMF, 0.092 g acetic acid, and 1.20 g sucrose-6-acetate. The resulting lower phase, designated the third lower phase, weighed 9.29 g and contained 3.68 g DMF, 0.06 g acetic acid, and 1.15 g sucrose-6-acetate.

It can thus be seen that the tendency to extract desirable sucrose-6-acetate from DMF into the extraction medium was very low, while the removal of acetic acid from the DMF was quite effective. Thus, methods of this invention provide excellent removal of acetic acid from DMF solutions of sucrose-6-acetate.

Example 2

Using a separatory funnel, a 101.7 g sample of the same stream used in Example 1 was extracted with 101.7 g of an extraction medium consisting of a 1:1 by weight mixture of trilaurylamine and dodecanol. The mixture was separated by centrifugation. The sample contained 71.9 g DMF, 4.7 g acetic acid, and 8.5 g sucrose-6-acetate. The resultant upper (extraction medium) phase weighed 111.2 g. The lower (DMF) phase weighed 86.9 g and was assayed to contain 62.3 g DMF, 1.6 g acetic acid, and 7.85 g sucrose-6-acetate. This is designated the first lower phase.

A 66.25 g portion of the first lower phase was extracted with 66.9 g of the 1:1 trilaurylamine:dodecanol mixture. The portion of 1$^{st}$ lower phase used contained 48.0 g DMF, 1.22 g acetic acid, and 6.04 g sucrose-6-acetate. The mixture was separated by centrifugation. The resulting lower phase, designated the second lower phase, weighed 56.6 g and contained 39.3 g DMF, 0.64 g acetic acid, and 6.16 g sucrose-6-acetate. The upper phase weighed 74.87 g.

A 39.16 g portion of the second lower phase was extracted with 39.0 g of the 1:1 trilaurylamine:dodecanol mixture. The portion of 2$^{nd}$ lower phase used contained 27.2 g DMF, 0.44 g acetic acid, and 4.26 g sucrose-6-acetate. The mixture was separated by centrifugation. The resulting lower phase, designated the third lower phase, weighed 33.38 g and contained 21.7 g DMF, 0.23 g acetic acid, and 4.18 g sucrose-6-acetate.

The reductions in amount of DMF in the lower phase were respectively 13%, 18%, and 20% at extractions 1, 2, and 3. The reductions of acetic acid in the lower phase were respectively 66%, 48%, and 48% at extractions 1, 2, and 3. The reductions in amount of sucrose-6-acetate in the lower phase were respectively 8%, −2% (a measured increase), and 2% at extractions 1, 2, and 3. It can thus be seen that the tendency to extract desirable sucrose-6-acetate into the extraction medium is minimal compared to acetic acid extraction, and thus the extraction can be used to separate acetic acid from sucrose-6-acetate. Similarly, DMF has a greater tendency to remain with the lower (aqueous) phase than does acetic acid, though not so great a tendency as sucrose-6-acetate. However, DMF losses may be minimized by returning the aqueous phase to the first extraction step, i.e., combined with the original feed stream, as discussed hereinabove.

Example 3

A description of a laboratory-scale extraction apparatus for use according to the invention will now be provided, followed by the results of exemplary DMF purifications performed with this apparatus.

Figure 3:
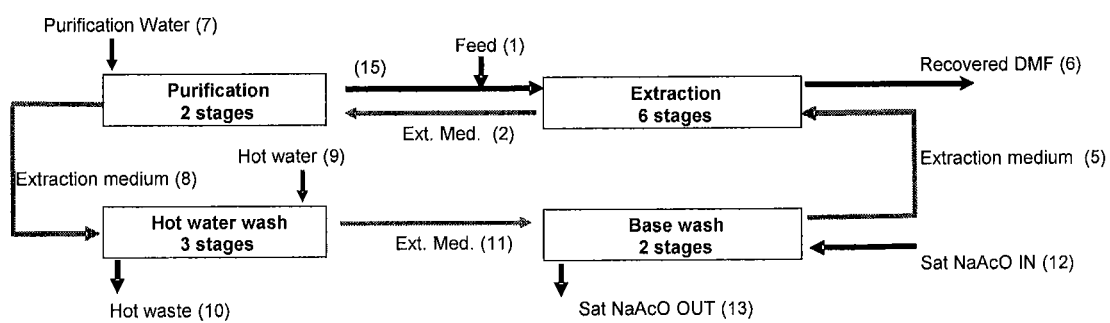
FIG. 3 is a schematic diagram of an extraction apparatus and process suitable for use according to the invention.

A laboratory version of a Robatel Model UX 1-1 (a 4-stage sequence of mixer-settlers, available from Rousselet-Robatel of Annonay, France) is used, having six mixer-settler stages operating in a counter current fashion in the extraction step and a similar two stages operating in the purification step. The purification step is connected to a hot water wash step comprising three counter current stages, which in turn is connected to a "base wash" step comprising two counter current stages. The extraction medium outlet of the base wash step is connected to the extraction stage—thus completing the return loop of the extraction medium phase. FIG. 3 is a representative schematic of the general process used.

The feed stream (1) is mixed with the heavy aqueous phase (15) exiting the purification step. This combined feed is mixed in a counter current fashion in the extraction step with extraction medium (5). This extraction step generates a "heavy phase" comprising the recovered DMF (6) as well as a "light phase" comprising the extraction medium (2) which now contains a substantial part of the carboxylic acids originally in the feed (1). The extraction step is typically conducted at a temperature between 25 and 35° C. The feed pH is typically about 6.5.

The acid-loaded extraction medium (2) is fed into the purification step, where it is contacted in a counter current fashion with purification water (7). The purpose of this step is to relieve the extraction medium of any residual DMF with minimal removal of the carboxylic acids. For this reason, the purification step is also carried out at temperatures close to ambient (25° C.). It is desirable to keep the temperature as low as possible without causing solidification of the extraction medium. As described previously, the heavy aqueous phase (15) exiting the purification step is combined with the feed stream (1)—in this way the maximum amount of DMF is recovered into stream (6). The light phase exiting the purification step (8) is the extraction medium phase, still loaded with carboxylic acids but substantially devoid of DMF.

This light extraction medium phase (8) is fed into the three-stage hot water wash step, where the extraction medium is contacted in a counter current fashion with hot water (9) at a target temperature of 80° C. This removes most of the carboxylic acids from the light extraction medium phase (11) and produces a heavy aqueous hot waste phase (10) containing much of the carboxylic acid.

In order to maximize the removal of carboxylic acids from the extraction medium, the light phase (11) from the hot water wash step is then fed into a base wash step. This comprises a two-stage counter current mixer settler, in which the extraction medium phase is contacted with saturated aqueous sodium acetate (12). This step serves two purposes: (i) it is pH adjusted to a high pH (ca. 11) in order to ensure that all the carboxylic acid moieties are in the anionic form (more water soluble) and (ii) the stream has a higher specific gravity to facilitate phase separation. In this step, further removal of carboxylic acids is achieved, leaving an extraction medium stream (5) from which the vast majority of the carboxylic acids has been removed. Waste aqueous sodium acetate (13) containing some carboxylic acid salts also exits the base wash step.

Using the above-described process and apparatus, extraction data were obtained as follows. A liquid stream comprising 85% DMF, 3.50% water and 6% acetic acid on a weight basis was fed into the extraction system at a rate of 4 g/minute. This stream was combined with the aqueous output from the purification step (about 2.7 g/min) and the combined feed was fed into the mixer settler extraction step where it was contacted in a counter current fashion with 12.5 g/min of the extraction medium phase, a mixture of dodecanol and trilaurylamine containing ca. 46% dodecanol and 43% trilaurylamine, the balance mostly consisting of water and of impurities present in the commercial grade amine and alcohol. Table 1 shows the conditions used for the extraction, and the results obtained. The inlet, outlet, and internal recycle streams are indicated as IN, OUT and INT respectively.

TABLE 1

| | Extraction step | | | | | |
|---|---|---|---|---|---|---|
| | Feed (1) | | Recovered DMF (6) | | Ext. Med. after Extraction (2) | |
| Flow g/min | % IN | g 3.96 | % OUT | g 6.61 | % INT | g 12.45 |
| DMF | 85% | 3.4 | 49.4% | 3.266 | 3.1% | 0.384 |
| Water | 3% | 0.1 | 44.3% | 2.925 | 1.5% | 0.186 |
| Dodecanol | 0% | 0.0 | 0.1% | 0.005 | 41.6% | 5.178 |

TABLE 1-continued

| | Extraction step | | | | | |
|---|---|---|---|---|---|---|
| | Feed (1) | | Recovered DMF (6) | | Ext. Med. after Extraction (2) | |
| Flow g/min | % IN | g 3.96 | % OUT | g 6.61 | % INT | g 12.45 |
| Trilaurylamine | 0% | 0.0 | 0.0% | 0.003 | 36.9% | 4.590 |
| Acetate | 6% | 0.2 | 0.2% | 0.012 | 1.6% | 0.203 |
| Formate | 0% | 0.0 | 0.0% | 0.000 | 0.0% | 0.000 |

Two streams exited the extraction step. The heavy phase (about 6.6 g/min) comprised 49% DMF, 44% water and about 0.2% acetic acid, corresponding to an acetate removal of about 95%. The light phase (extraction medium phase) exited the extraction step at a rate of about 12.5 g/min and contained 3% DMF, 1.50% water, 42% dodecanol and 37% trilaurylamine, as well as 1.6% acetate.

The light (extraction medium) phase was then continuously fed to a purification step where it contacted purification water being fed in a counter current fashion at a rate of 2.7 g/min. See Table 2. The extraction medium phase exited the purification step at a rate of ca. 12.5 g/min and comprised 1.9% DMF, 1.6% water, 46% dodecanol and 41% trilaurylamine, along with 1.6% acetate (measured as acetate ion, using an ion analyzer available from Dionex Corporation of Sunnyvale, Calif.).

TABLE 2

| | Purification step | | | |
|---|---|---|---|---|
| | Flow g/min | | | |
| | Ext. Med. after Purification (8) | | Purification water (7) | |
| | % INT | g 12.45 | % IN | g 2.71 |
| DMF | 1.9% | 0.236 | 0.0% | 0.000 |
| Water | 1.6% | 0.199 | 100.0% | 2.710 |
| Dodecanol | 46.2% | 5.758 | 0.0% | 0.000 |
| Trilaurylamine | 40.8% | 5.082 | 0.0% | 0.000 |
| Acetate | 1.6% | 0.197 | 0.0% | 0.000 |
| Formate | 0.0% | 0.000 | 0.0% | 0.000 |

As shown below in Table 3, the resulting purified extraction medium phase was fed into a hot water wash step (three-stage mixer settler) at a rate of ca. 12.5 g/min, where it was contacted in a counter current fashion with hot water being fed at a rate of 42 g/min. The hot water-washed extraction medium exited at a rate of ca. 12.5 g/min and contained 1.0% DMF and 0.40% acetate. The hot water exited as a waste at ca. 42 g/min, and contained 0.5% acetate. Thus, the hot water wash removed 75-80% of the acetate in the extraction medium.

After the hot water wash, the extraction medium was fed at a rate of 12.5 g/min to the base water wash where it was contacted in a counter current fashion with an aqueous saturated sodium acetate stream at a pH of 11.5. The base wash was fed at a rate of 12.5 g/min and the pH of this stream on exiting the base water wash step was about 10.8, the reduction being due to the uptake of some carboxylic acid into the aqueous phase. The extraction medium phase (5) exited the base wash step at a rate of 12.5 g/min and contained 46% dodecanol and 43% trilaurylamine.

TABLE 3

| | Hot water wash and base wash | | | | | |
|---|---|---|---|---|---|---|
| | Hot water | | Waste wash water | | Ext. Med. After hot wash. | |
| Flow g/min | % IN | g 41.8 | % OUT | g 41.7 | % INT | g 12.45 |
| DMF | 0.0% | 0.000 | 0.4% | 0.167 | 1.0% | 0.125 |
| Water | 100.0% | 41.800 | 99.8% | 41.617 | 1.4% | 0.168 |
| Dodecanol | 1.0% | 0.418 | 0.0% | 0.000 | 45.0% | 5.602 |
| Trilaurylamine | 0.0% | 0.000 | 0.0% | 0.000 | 54.7% | 6.808 |
| Acetate | 0.0% | 0.000 | 0.5% | 0.198 | 0.4% | 0.047 |
| Formate | 0.0% | 0.000 | 0.0% | 0.000 | 0.0% | 0.000 |

As can be seen from the above data, 95% of the acetic acid present in the incoming feed was removed, with little loss of DMF. It will be apparent to those skilled in the art that further optimisation of this process is possible with the addition of extra stages in different steps, further optimization and control of temperatures and pH etc.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method of removing a carboxylic acid from a liquid comprising a tertiary amide solvent, the method comprising a step of contacting the liquid comprising the tertiary amide solvent and the carboxylic acid with an extraction medium comprising an amine that is immiscible with both water and the tertiary amide solvent, thereby forming a phase comprising de-acidified tertiary amide solvent and a phase comprising the extraction medium and the carboxylic acid.

2. The method of claim 1, wherein the tertiary amide solvent is dimethyl formamide.

3. The method of claim 1, additionally comprising a step of treating the de-acidified tertiary amide solvent to further purify it.

4. The method of claim 3, wherein the step of treating comprises distilling or evaporating and condensing the tertiary amide solvent.

5. The method of claim 1, wherein the amine is a monoamine not comprising any heteroatoms other than the nitrogen atom of the amine.

6. The method of claim 1, wherein the amine is a tertiary amine.

7. The method of claim 1, wherein the amine is according to the formula $NR^1R^2R^3$ where each of $R^1$, $R^2$ and $R^3$ is independently selected from the group consisting of H and $C_1$-$C_{20}$ linear or branched alkyl, cyclic, alicyclic, alkenyl, aryl, aralkyl, and alkaryl groups, provided that at least one of $R^1$, $R^2$ and $R^3$ is not H.

8. The method of claim 7, wherein the total number of carbon atoms in $R^1$, $R^2$ and $R^3$ combined is at least 24.

9. The method of claim 1, wherein the amine comprises trilaurylamine.

10. The method of claim 1, wherein the amine does not have a boiling point lower than that of the tertiary amide solvent.

11. The method of claim 1, wherein the amine has a melting point of at most 20° C.

12. The method of claim 1, wherein the extraction medium comprises a mixture of the amine with a water-immiscible alcohol $R^1OH$, wherein $R^1$ is a $C_7$-$C_{20}$ hydrocarbyl group.

13. The method of claim 12, wherein the water-immiscible alcohol comprises dodecanol.

14. The method of claim 1, wherein the carboxylic acid comprises acetic acid, formic acid, or a mixture of these.

15. The method of claim 1, further comprising the steps of
washing the phase comprising the extraction medium and the carboxylic acid with water at a temperature in a range from 10° C. to 40° C. to form a purified extraction medium;
washing the purified extraction medium with water at a temperature in a range from 50° C. to 90° C. to give a partially de-acidified extraction medium; and
washing the partially de-acidified extraction medium with an aqueous base to give a substantially de-acidified extraction medium.

16. The method of claim 1, wherein the tertiary amide solvent constitutes at least 60 wt % of the liquid.

17. The method of claim 1, further comprising forming a solution of sucrose in the resulting tertiary amide solvent and subsequently converting the sucrose to sucralose.

18. The method of claim 17, wherein said converting comprises converting the sucrose to a sucrose-6-acylate and subsequently converting the sucrose-6-acylate to sucralose.

19. The method of claim 18, wherein the sucrose-6-acylate is sucrose-6-acetate.

20. The method of claim 1, wherein both the liquid comprising the tertiary amide solvent and the phase comprising de-acidified tertiary amide solvent further comprise a sucrose-6-acylate.

21. The method of claim 20, further comprising converting the sucrose-6-acylate to sucralose.

22. The method of claim 20, wherein the sucrose-6-acylate is sucrose-6-acetate.

* * * * *